United States Patent
Oriou et al.

(10) Patent No.: US 12,042,553 B2
(45) Date of Patent: Jul. 23, 2024

(54) CLEANSING COMPOSITION

(71) Applicant: Conopco, Inc., Englewood Cliffs, NJ (US)

(72) Inventors: Jules Oriou, Wirral (GB); Pierre Starck, Chester (GB); Shubhalaxmi Madhukar Thaokar, Mumbai (IN); Paul Stephen Whitehead, Birkenhead (GB)

(73) Assignee: Conopco, Inc., Englewood Cliffs, NJ (US)

( * ) Notice: Subject to any disclaimer, the term of this patent is extended or adjusted under 35 U.S.C. 154(b) by 266 days.

(21) Appl. No.: 17/772,790

(22) PCT Filed: Nov. 10, 2020

(86) PCT No.: PCT/EP2020/081680
§ 371 (c)(1),
(2) Date: Apr. 28, 2022

(87) PCT Pub. No.: WO2021/094334
PCT Pub. Date: May 20, 2021

(65) Prior Publication Data
US 2022/0409509 A1    Dec. 29, 2022

(30) Foreign Application Priority Data

Nov. 11, 2019  (IN) .............................. 201921045863
Jan. 23, 2020  (EP) .................................... 20153477

(51) Int. Cl.
| | |
|---|---|
| A61K 8/00 | (2006.01) |
| A61K 8/20 | (2006.01) |
| A61K 8/23 | (2006.01) |
| A61K 8/46 | (2006.01) |
| A61K 8/81 | (2006.01) |
| A61K 8/898 | (2006.01) |
| A61Q 5/02 | (2006.01) |
| A61Q 19/10 | (2006.01) |

(52) U.S. Cl.
CPC ................ *A61K 8/466* (2013.01); *A61K 8/20* (2013.01); *A61K 8/23* (2013.01); *A61K 8/817* (2013.01); *A61K 8/898* (2013.01); *A61Q 5/02* (2013.01); *A61Q 19/10* (2013.01)

(58) Field of Classification Search
None
See application file for complete search history.

(56) References Cited

U.S. PATENT DOCUMENTS

| | | |
|---|---|---|
| 5,811,087 A | 9/1998 | Mohring et al. |
| 2012/0157365 A1 | 6/2012 | Fevola |
| 2016/0095804 A1 | 4/2016 | Xavier et al. |
| 2017/0079899 A1 | 3/2017 | Li et al. |
| 2017/0095410 A1 | 4/2017 | Hara et al. |
| 2017/0319453 A1 | 11/2017 | Ando |
| 2017/0340540 A1 | 11/2017 | Darras et al. |
| 2017/0360688 A1 | 12/2017 | Fevola et al. |
| 2019/0314258 A1 | 10/2019 | Laurent et al. |

FOREIGN PATENT DOCUMENTS

| | | |
|---|---|---|
| CN | 107519094 | 12/2017 |
| CN | 107530243 | 1/2018 |
| WO | WO2018002557 | 1/2018 |
| WO | WO2020254318 | 12/2020 |

OTHER PUBLICATIONS

Search Report and Written Opinion in EP20153477; Jul. 13, 2020; European Patent Office (EPO).
Database GNPD (Online) Mintel; Shampoo; Ogx Fade-Defying + Orchid Oil; May 2016; pp. 1-3, XP055505461, Record ID 3998067; United States of America.
Database BNPD (Online) Mintel; Shea Moisturizing Body Wash; Tree Hut Hawaiian Kukui ; Jul. 2, 2019; PP1-3 XP055505461, Record ID 6679301.
Search Report and Written Opinion in PCTEP2020081680; Dec. 21, 2020; World Intellectual Property Org. (WIPO).
IPRP2 in PCTEP2020081680; Nov. 2, 2021; World Intellectual Property Org. (WIPO).

*Primary Examiner* — Necholus Ogden, Jr.
(74) *Attorney, Agent, or Firm* — Foley & Lardner LLP

(57) ABSTRACT

A sulphate-free-surfactant cleansing composition comprising, in an aqueous continuous phase: a total amount of anionic surfactant and amphoteric surfactant consisting of: (i) from 3 wt % to 13 wt %, by weight of the total composition at 100% activity, of an alpha olefin sulfonate anionic surfactant of general formula (I): $R^1$—CH=CH—$CH_2$—$SO_3$-$M^+$ (I) in which $R^1$ is selected from linear or branched alkyl groups having from 11 to 13 carbon atoms and mixtures thereof; and M is a solubilizing cation; (ii) from 1 to 8 wt %, by weight of amphoteric surfactant, which is cocamidopropyl betaine; (iii) from 0.05 wt % to 0.5 wt % of a cationic polymer; (iv) from 0.3 to 2.8 wt % an inorganic electrolyte; and (v) water; in which the weight ratio of (i) to (ii) ranges from 2:1 to 1:4 and the pH of the composition is from 3 to 6.5; and wherein the composition has a viscosity of from 2,500 to 25,000 mPa·s, when measured using a TA Instruments Discovery Hybrid Rheometer; parallel 40 mm sandblasted plates, peak hold protocol at 4 $s^{-1}$; at 30° C.

13 Claims, No Drawings

CLEANSING COMPOSITION

CROSS REFERENCE TO RELATED APPLICATIONS

The present application is a U.S. National Phase Application under 35 U.S.C. § 371 of International Application No. PCT/EP2020/081680, filed on Nov. 10, 2020, which claims priority to Indian Application No. 201921045863 filed Nov. 11, 2019, and European patent application No. 20153477.3 filed on Jan. 23, 2020, the contents of each of which are incorporated by reference herein in their entireties.

FIELD OF THE INVENTION

The subject invention relates to mild sulphate-free-surfactant cleansing compositions, particularly for hair and skin, including scalp.

BACKGROUND AND PRIOR ART

Microstructure and rheology are important factors in personal care formulations, as they affect consumer acceptance as well as product performance. The selection, amount and relative amount of surfactant contributes to the microstructure of a personal cleansing composition. In turn, microstructure can impact rheological properties such as composition viscosity and viscosity building characteristics and may also contribute to composition stability.

A sufficient level of surfactant is ordinarily needed for surfactant molecules to be able to assemble into micelles, and for the micelles to aggregate to build structure. Commercially available water-based cleansing compositions frequently contain upwards of 12 weight percent of surfactant. The major surfactant component of such compositions is commonly an alkyl and/or alkyl ether sulfate surfactant, with lauryl and laureth sulfates, surfactants known to afford good detergency, being among the sulfate surfactants commonly employed. Sulfate surfactants belong to a class of materials known as anionic surfactants. The sulfate surfactants are frequently used together with an amphoteric co-surfactant, with betaine surfactants such as cocamidopropyl betaine being among the amphoteric surfactants commonly employed. Betaine surfactants help to boast lather and are generally milder than sulfate surfactants, albeit without the detergent power of the sulfate surfactants. Advantageously, personal cleansing compositions based on sulfate surfactant can normally be thickened by the addition of simple salts.

Despite the widespread use of sulfate surfactants in personal cleansing compositions, there is considerable interest in milder alternatives, including compositions in which the anionic surfactant is a sulfate free surfactant.

Achieving an acceptable composition viscosity is an important factor in providing a mild personal cleansing composition that can be applied in a controlled manner and readily spread in use. Composition viscosity, together with attributes such as foamability can also impact consumer perception of such products. When sulfate surfactants are eliminated, developing a microstructure that results in desirable rheological properties can be challenging, particularly in the case of mild compositions with low surfactant concentrations; additionally, building the viscosity of such compositions by the addition of a simple salt can be problematic. Eliminating sulfate surfactants can also be problematic in regard to formulating mild cleansing compositions that are stable at acidic pH.

One approach to the issue of thickening systems that are free of sulfate surfactants has been to use sulfate-free surfactants together with polymeric thickeners. Polymeric thickeners can have a gelation effect that transforms a product with what is ordinarily Newtonian rheology under conditions of low shear, such as is experienced, for example, during dosing, application and spreading in-use, to a non-Newtonian rheology. In addition to being detectable by a consumer as an undesirable departure from product norms, the use of such thickeners can further limit the ability to subsequently adjust composition viscosity through the use of simple salts.

Employing relatively high levels of non-sulfate surfactant may also assist in building the viscosity of systems that are free of sulfate surfactants. The levels of non-sulfate surfactant needed may, however, be higher than conventional norms, and may also result in non-isotropic surfactant systems having relatively non-labile liquid crystalline structures or domains. In contrast to isotropic surfactant systems, which tends to promote foaming efficiency, the relatively labile microstructure of liquid crystalline microstructures tend to "trap" surfactant and impair foamability. Additionally, liquid crystalline structures or domains may impede light transmission and may impart a turbid or cloudy appearance to a composition, which may be problematic where translucency is desired.

There is a need for mild cleansing compositions, that utilise sulphate free surfactants, suitable for hair, skin and scalp, having desirable rheological properties, including compositions with relatively low surfactant concentrations. Of particular interest are low surfactant content compositions free of sulfate surfactants, the viscosity of which compositions may be increased through the addition of electrolytes such as simple salts.

WO18002557A1 uses high concentrations (35-60%) of surfactant mixtures including sulfate free anionic, amphoteric and non-ionic that access the lamellar phase region to control the rheology. These formulas have no added salt. Although high surfactant concentrations in lamellar phase solve the rheology build problem, they may not favour mild benefits or have the in-use application and sensory characteristics of an isotropic shampoo, such as transparent appearance and flash foam.

US2017319453A teaches that a combination of Alpha Olefin Sulfonate (AOS) plus a glycerin fatty acid ester and an amphoteric surfactant (a betaine) give no irritation or reduced irritation, and superior foam quality, and may be stable, in particular stable over time and/or under elevated temperature. Under acidic pH, ester bonds are prone to attack and can become unstable, which tends to thin an isotropic formula over time. Heat will accelerate these destabilising reactions.

US2016095804A uses complex combinations of sulfate free surfactants (e.g. anionic surfactant plus amphoteric surfactants with optional non-ionic surfactants) but structures them with hydrophobically modified, high molecular weight polymers. It also employs cationic conditioning agents (mixtures of polymers and silicones or functional silicones). However, we have found that the addition of structuring polymers to a cleansing formula can result in adverse sensory performance in the form of poor clean feel, coating and stickiness.

US2017079899A & US2017095410A reveal that blends of Alpha Olefin Sulfonate with different chain lengths (C16+ C18) at high concentrations and at specific ratios require a suspending agent in the form of a polymeric material to thicken the formula. The use of amphoteric or zwitterionic materials such as betaines and the inclusion of at least one foam booster such as a fatty material are also envisaged.

US2012157365A uses a mixture of polyglyceryl nonionic, amphoteric and sulfate free anionic surfactants at pH less than 5.4 to employ organic acids such as sodium benzoate as the preservative. Ratios of polyglyceryl to amphoteric range from 0.05:1 to 3:1 and sulfate free anionic to amphoteric ranges from 0.3:1 to 4:1.

U.S. Pat. No. 5,811,087 discloses aqueous hair shampoos containing a combination of a) 1% to 25% wt. of at least one alkyl amidoether carboxylic acid of a defined formula; b) 1% to 25% wt. of at least one anionic sulfate or sulfonate surfactant; c) 0.1% to 10% wt. of at least one compound selected from C8-C18-acylmono-and-dialkanolamides, surface-active betaines and sulfobetaines and (or) surface-active amine oxides; and d) 0.05% to 5% by wt. of at least one cationic polymer, having a charge density of at least 2.50 meq/g. An example includes alpha olefin sulphonate and lauryl hydroxy sultaine.

US2017/0340540 discloses cosmetic compositions, for cleansing and caring for keratinous substrates, comprising: (i) one or more linear alpha-olefin sulfonates, (ii) one or more non-oxyalkylenated anionic surfactants other than the compounds (i), present at 1% to 20% by weight; and (iii) one or more additional surfactants chosen from amphoteric surfactants and nonionic surfactants. An example includes alpha olefin sulphonate and cocobetaine along with 0.5 wt % of polyquaternium-10.

US2017/0360688 reveals the use of a combination of anionic and cationic polyelectrolytes in cosmetic compositions also containing at least one surfactant. Stable viscosity and yield stress are achieved.

The inventors have identified Alpha Olefin Sulfonate (AOS) as a sulfate free, primary surfactant. As with sulfate based chassis a secondary surfactant is required to help build viscosity using salt, control the foam and aid in the delivery of mildness benefits through lower CMC.

It is desirable to reduce the level of surfactant used in formulations (for mildness and environmental benefits). We have found, however, that if you reduce the amount of surfactant, then the viscosity of the formulation falls undesirably.

In previous studies, it has been found that a secondary surfactant, cocamidopropyl betaine (CAPB) does not allow viscosity to be built at low total surfactant concentrations with Alpha Olefin Sulfonate (AOS) as the primary surfactant.

However, the inventors have now found that, surprisingly, a combination, of AOS with cocoamidopropyl betaine, at a specific defined ratio, can afford viscosity builds with salt addition at low total concentrations of surfactant. This negates the need for other thickening agents, for example, polymers and other secondary surfactants.

Compositions in accordance with the invention having a combination of anionic and cocamidopropyl betaine at enriched cocamidopropyl betaine ratios; reduced surfactant concentrations; specific primary sulfate free surfactant levels and a cationic polymer, gives good foamability, excellent cleaning, wet detangling and desirable rheological characteristics, whilst maintaining mildness to skin and hair protein.

DEFINITION OF THE INVENTION

In a first aspect the present invention provides a sulphate-free-surfactant cleansing composition comprising, in an aqueous continuous phase:

a total amount of sulphate free anionic surfactant and sulphate free amphoteric surfactant, consisting of:
(i) from 3 wt % to 13 wt %, by weight of the total composition at 100% activity, of an alpha olefin sulfonate anionic surfactant of general formula (I):

$$R^1-CH=CH-CH_2-SO_3^-M^+ \qquad (I)$$

in which $R^1$ is selected from linear or branched alkyl groups having from 11 to 13 carbon atoms and mixtures thereof; and M is a solubilizing cation;
(ii) from 1 to 8 wt %, by weight of amphoteric surfactant, which is cocamidopropyl betaine;
(iii) from 0.05 wt % to 0.5 wt % of a cationic polymer;
(iv) from 0.3 to 2.8 wt % an inorganic electrolyte; and
(v) water;
in which the weight ratio of (i) to (ii) ranges from 2:1 to 1:4 and the pH of the composition is from 3 to 6.5; and
wherein the composition has a viscosity of from 2,500 to 25,000 mPa·s, when measured using a TA Instruments Discovery Hybrid Rheometer (parallel 40 mm sand-blasted plates, peak hold protocol at 4 s$^{-1}$) at 30° C.

In a second aspect, the invention provides a method of treating hair and/or scalp and/or skin comprising the step of applying to the hair and/or scalp and/or skin a composition as defined by the first aspect.

Preferably the method comprises an additional step of massaging the composition of the first invention into the hair and/or scalp and/or skin.

Preferably the method comprises an additional step of rinsing the hair and/or scalp and/or skin.

DETAILED DESCRIPTION OF THE INVENTION

All molecular weights as used herein are weight average molecular weights, unless otherwise specified.

Aqueous Continuous Phase

By "aqueous continuous phase" is meant a continuous phase which has water as its basis.

Suitably, the composition of the invention will comprise from about 75 to about 95%, preferably from 85 to 95%, more preferably from 87 to 95% water (by weight based on the total weight of the composition).

Preferably the composition comprises an isotropic surfactant phase, where under dilution, isotropic micelles provide higher availability of monomers to the air/water interface, whereas anisotropic may diffuse at a slower rate, resulting in lower flash foam properties. Thus, the isotropic phase is advantageous for product appearance, clarity and good flash foam properties.

All amounts referred to herein are based on 100% activity (or "active") unless otherwise stated. By 100% activity (or "active") is meant that the material is not diluted and is at 100% v/v or wt/wt. Many materials used in personal care formulations are commercially available at different active concentrations, for example at 70% active or 60% active. For example, 100 ml of 70% active surfactant provides the same amount of active material as 70 ml of 100% active surfactant. Therefore, in order to provide for variations in activities of materials, all amounts are based on 100% active materials.

The aqueous continuous phase comprises a total amount of anionic, amphoteric and zwitterionic surfactant consisting of (i) and (ii) below. That is to say, no further anionic, amphoteric and zwitterionic surfactants are present in the compositions of the invention.

Preferably, no other surfactants, for example, nonionic surfactants are present in the compositions of the invention.

(i) The Alpha Olefin Sulfonate Anionic Surfactant

The composition of the invention comprises (i) one or more alpha olefin sulfonate anionic surfactants of general formula (I)

$$R^1—CH=CH—CH_2—SO_3^-M^+ \quad (I)$$

in which $R^1$ is selected from linear or branched alkyl groups having from 11 to 13 carbon atoms and mixtures thereof; and M is a solubilizing cation;

Preferably $R^1$ in general formula (I) is a $C_{14}$ or $C_{16}$ linear alkyl group.

Preferably M in general formula (I) is selected from alkali metal cations (such as sodium or potassium), ammonium cations and substituted ammonium cations (such as alkylammonium, alkanolammonium or glucammonium).

Commercially produced alpha olefin sulfonate anionic surfactants of general formula (I) may be made by sulfating C14-16 olefins derived from natural gas. The process can also yield mixtures of homologues and low levels of unreacted olefins.

Particularly preferred is alpha olefin sulfonate with an average of 14-16 carbons. A suitable example of such a material is Bioterge AS40 (ex Stepan).

The amount of alpha olefin sulfonate anionic surfactant, at 100% activity, of general formula (I) ranges from 3 to 13%, for example from 3 to 12.85%, preferably from 3.5 to 12%, more preferably from 3 to 10%, still more preferably from 3 to 9% and most preferably from 3.25 to 8% (by weight based on the total weight of the composition).

(ii) The Amphoteric Surfactant-Cocamidopropyl Betaine

The composition of the invention comprises cocamidopropyl betaine.

A suitable example is available under the tradename Tego betain CK KB5, ex Evonik.

The cocamidopropyl betaine is present in an amount of from 1 to 8 wt %.

The combined amount of (i) and (ii) ranges from 5 to 19 wt %, preferably from 7 to 15 wt %, most preferably from 8 to 14 wt % (based on the total weight of the composition and 100% activity).

The weight ratio of the alpha olefin sulfonate anionic surfactant (i) to the amphoteric surfactant (ii) ranges from 2:1 to 1:4, preferably 2:1 to 1:3, and most preferably 2:1 to 1:1.

The pH of the composition of the invention ranges from 3 to 6.5, preferably from 3.5 to 5.1, more preferably from 4 to 5.

A protonating agent may be used for achieving the low pH. Suitable protonating agents are acids. Suitable acids useful herein include hydrochloric acid, citric acid, acetic acid, tartaric acid, fumaric acid, lactic acid, malic acid, succinic acid, and mixtures thereof. Preferably, the acid is selected from the group consisting of citric acid, acetic acid, tartaric acid, hydrochloric acid, fumaric acid, lactic acid and mixtures thereof.

(iii) The Cationic Polymer

The composition of the invention comprises (iii) one or more cationic polymers. Such polymers may enhance the delivery of wet feel benefits in the composition.

Cationic polymers for use in the invention suitably have a cationic charge density ranging from about 0.3 to about 4 meq/g, preferably from about 0.4 to about 3.5 meq/g. The term "cationic charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain. Cationic charge density can be determined according to the Kjeldahl Method. Those skilled in the art will recognize that the charge density of amino-containing polymers may vary depending upon pH and the isoelectric point of the amino groups. The charge density should be within the above limits at the pH of intended use.

Suitable cationic polymers for use in the invention include cationic polysaccharide derivatives, such as cationic cellulose derivatives, cationic starch derivatives, and cationic guar gum derivatives.

Preferred cationic polysaccharide derivatives for use in the invention include cationic guar gum derivatives and cationic cellulose derivatives.

Examples of preferred cationic guar gum derivatives for use in the invention include guar hydroxypropyltrimethylammonium chlorides. Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl) trimethylammonium chloride.

Guar hydroxypropyltrimethylammonium chlorides for use in the invention generally have an average molecular weight (weight average molecular mass ($M_w$) determined by size exclusion chromatography) in the range 500,000 to 3 million g/mol, more preferably 800,000 to 2.5 million g/mol.

Guar hydroxypropyltrimethylammonium chlorides for use in the invention (preferably guar hydroxypropyltrimethylammonium chlorides) generally have a charge density ranging from 0.5 to 1.8 meq/g.

Examples of preferred cationic cellulose derivatives for use in the invention include poly(1,2-oxyethanediyl)-2-hydroxy-3-trimethylammonium propyl chloride cellulose ethers (INCI: Polyquaternium-10).

Preferably, the cationic polymer is selected from Polyquaternium 10, guar hydroxypropyltrimethylammonium chlorides having a $M_w$ ranging from 800,000 to 2.5 million g/mol and a charge density ranging from 0.5 to 1.8 meq/g, and mixtures thereof.

Mixtures of any of the above described cationic polymers may also be used.

In a typical composition according to the invention the amount of cationic polymer will generally range from 0.05 wt % to 0.5 wt % and preferably ranges from 0.15 wt % to 0.5 wt % based on the total weight of the composition.

In a preferred composition according to the invention the one or more cationic polymers are selected from guar hydroxypropyltrimethylammonium chlorides having a $M_w$ ranging from 800,000 to 2.5 million g/mol and a charge density ranging from 0.5 to 1.8 meq/g; in an amount ranging from 0.15 to 0.3% (by weight based on the total weight of the composition).

Another class of suitable cationic conditioning polymers are the high molecular weight Polyethylene Glycol (PEG) polymers, for example PEG 45M, available as Polyox from Dow.

Mixtures of any of the above described polymers may also be used.

The Inorganic Electrolyte

We have found that, surprisingly, the compositions of the invention are amenable to building viscosity very well. It is thus possible to build viscosity at lower concentrations at enriched surfactant ratios. This is further advantage of the invention.

The composition of the invention includes at least one inorganic electrolyte. The inorganic electrolyte provides viscosity to the composition.

The viscosity of the composition suitably ranges from 2,500 to 25,000 mPa·s, preferably from 3,000 to 20,000 mPa·s, more preferably from 3,500 to 20,000 mPa·s, even more preferably from 3,500 to 15,000 mPa·s, most preferably from 4,000 to 12,000 mPa·s. A suitable method of measuring the viscosity is to use a TA Instruments Discovery Hybrid Rheometer (parallel 40 mm sandblasted plates, peak hold protocol at 4 s$^{-1}$) at 30° C.

At these range our products are pourable yet thick enough to satisfy the consumer desire for thick compositions.

Suitable inorganic electrolytes include metal chlorides (such as sodium chloride, potassium chloride, calcium chloride, magnesium chloride, zinc chloride, ferric chloride and aluminium chloride) and metal sulfates (such as sodium sulfate and magnesium sulfate).

It is intended that the inorganic electrolyte is separate from any inorganic electrolytes that may be present in the raw materials of the invention.

Examples of preferred inorganic electrolytes for use in the invention include sodium chloride, potassium chloride, magnesium sulfate and mixtures thereof.

Mixtures of any of the above described materials may also be suitable.

The amount of inorganic electrolyte in compositions of the invention preferably ranges from 0.3 to 2.8%, more preferably from 0.5 to 2.5%, most preferably from 0.5 to 2.3% (by weight based on the total weight of the composition).

A preferred composition of the invention has a weight ratio of (i) an alpha olefin sulfonate anionic surfactant of general formula (I) to (ii) cocamidopropyl betaine, of from 2:1 to 1:1 and comprises an amount of inorganic electrolyte of from 0.5 to 23 wt % based on total weight of the composition.

Preferably, the compositions of the invention are free from silicone. In the context of the invention, by free from is meant having less than 0.4 weight %, more preferably less than 0.1 weight %, even more preferably less than 0.05 weight %, still more preferably less than 0.001 weight %, yet preferably less than 0.0001 weight %, and most preferably 0 weight % of silicone by weight of the total composition.

Preferably, the compositions of the invention are free from additional thickening agents selected from thickening polymers (preferably selected from hydroxy ethyl cellulose, and associative thickening polymers) and visco-surfactants (preferably cocoamide monoethanolamine (CMEA). In the context of the invention, by free from is meant having less than 0.4 weight %, more preferably less than 0.1 weight %, even more preferably less than 0.05 weight %, still more preferably less than 0.001 weight %, yet preferably less than 0.0001 weight %, and most preferably 0 weight % of thickening agents by weight of the total composition. For the sake of clarity, the cationic polymer (iii) of the invention is not intended to be a thickening polymer.

Most preferably, the compositions of the inventions are free from silicones and free from thickening agents as defined above.

Preferably, the composition is transparent. Where the composition is transparent, it is free from materials that cause cloudiness, such as silicones, structurants (for example carbomer) and visco-surfactants (for example cocoamide monoethanolamide (CMEA)). In the context of the invention, by free from materials that cause cloudiness is meant having less than 0.4 weight %, more preferably less than 0.1 weight %, even more preferably less than 0.05 weight %, still more preferably less than 0.001 weight %, yet more preferably less than 0.0001 weight % and most preferably 0 weight %, of materials that cause cloudiness, by weight of the total composition, such that a transparent composition in obtained.

A Preservative

The composition of the invention preferably comprises one or more preservatives, selected from sodium benzoate, sodium salicylate, benzyl alcohol, phenoxyethanol, 1,2-alkanediols, Iodopropynyl butylcarbamate (IPBC), 5-chloro-2-methyl-2H-isothiazol-3-one, 2-methyl-2H-isothiazol-3-one, or mixtures thereof. Preferably the preservative is an organic acid, most preferably the preservative is sodium benzoate.

A preferred composition has a pH of from 3 to 5, preferably 4 to 5 and comprises a preservative that is sodium benzoate.

Optional Ingredients

Preferably, the composition of the invention further comprises one or more structurants to assist in the suspension of dispersed benefit agent and provide phase stability. Suitable structurants include polyacrylic acids, polymethacrylic acids, cross-linked polymers of acrylic acid, cross-linked polymers of methacrylic acid, copolymers of acrylic acid with a hydrophobic monomer, copolymers of methacrylic acid with a hydrophobic monomer, copolymers of carboxylic acid-containing monomers and acrylic esters, copolymers of carboxylic acid-containing monomers and methacrylic esters, cross-linked copolymers of acrylic acid and acrylate esters, cross-linked copolymers of methacrylic acid and acrylate esters heteropolysaccharide gums and crystalline long chain acyl derivatives.

Preferred structurants are selected from polyacrylic acids, polymethacrylic acids, cross-linked polymers of acrylic acid, cross-linked polymers of methacrylic acid and mixtures thereof.

Mixtures of any of the above structurants may be used.

When included, the total amount of structurant is generally 0.1 to 10%, preferably from 0.1 to 3%, more preferably from 0.2 to 2%, most preferably from 0.3 to 0.9% (by weight based on the total weight of the composition).

A preferred composition comprises a structurant selected from polyacrylic acids, polymethacrylic acids, cross-linked polymers of acrylic acid, cross-linked polymers of methacrylic acid and mixtures thereof in an amount of from 0.1 to 10%, preferably from 0.1 to 3%, more preferably from 0.2 to 2%, most preferably from 0.3 to 0.9% (by weight based on the total weight of the composition).

A composition of the invention may contain further optional ingredients to enhance performance and/or consumer acceptability. Examples of such ingredients include fragrance, dyes and pigments. Each of these ingredients will be present in an amount effective to accomplish its purpose. Generally, these optional ingredients are included individually at an amount of up to 5% (by weight based on the total weight of the composition).

The composition of the invention is primarily intended for topical application to the hair, scalp or skin.

Most preferably the composition of the invention is topically applied to the hair, scalp or skin and then massaged into the hair, scalp or skin. The composition is then rinsed off the hair, scalp or skin with water prior to drying the hair, scalp or skin.

All amounts herein are given as weight percent, by total weight of the composition, unless otherwise stated.

The invention will be further illustrated by the following, non-limiting Examples.

EXAMPLES

Example 1: Preparation of Compositions 1 to 9 in Accordance with the Invention and Comparative Composition A Rinse-off aqueous hair cleansing shampoo formulations were prepared, having ingredients as shown in Table 1 below.

All the shampoos were prepared using the following method:
1. A vessel was charged with water. Surfactants and any structurant were added with stirring.
2. The mixture was heated to 30° C. and mixed until completely homogenous.
3. Any cationic polymer was then added and mixed well.
4. Any preservative was added.
5. The pH was adjusted to pH 4.5 using citric acid.
6. Salt was then added to adjust the viscosity.

TABLE 1

Compositions 1 to 6 in accordance with the invention and Comparative Composition A.

| INCI and/or Trade Name | % active | A (8% 3:1) | 1 (14% 2:1) | 2 (8% 2:1) | 3 (8% 1:2) | 4 (12% 1:2) | 5 (10% 1:3) | 6 (12% 2:1) |
|---|---|---|---|---|---|---|---|---|
| Alpha Olefin Sulfonate | 38.5 | 15.58 | 24.23 | 13.77 | 6.94 | 10.39 | 6.49 | 20.78 |
| Cocamidopropyl betaine | 30 | 6.67 | 15.57 | 8.9 | 17.67 | 26.67 | 25 | 13.33 |
| Polyquaternium 10 | 100 | 0.2 | 0.2 | 0.2 | 0.2 | 0.2 | 0.2 | 0.2 |
| Perfume | 100 | 0.55 | 0.55 | 0.55 | 0.55 | 0.55 | 0.55 | 0.55 |
| Preservative | 100 | 0.5 | 0.5 | 0.5 | 0.5 | 0.5 | 0.5 | 0.5 |
| Citric acid | 100 | to pH 4.5 | to pH 4.5 | to pH 4.5 | to pH 4.5 | to pH 4.5 | to pH 4.5 | to pH 4.5 |
| Sodium Chloride | 100 | 2.5 | 1 | 2 | 0.5 | 0.5 | 0.5 | 1.5 |
| Water | 100 | to 100% | to 100% | to 100% | to 100% | to 100% | to 100% | to 100% |

Example 2: Viscosity Properties of Compositions 1 to 9 in Accordance with the Invention and Comparative Composition A The viscosities of the compositions given in Table 1 were measured using a TA Instruments Discovery Hybrid Rheometer (parallel 40 mm sandblasted plates, peak hold protocol at 4 s$^{-1}$) at 30° C. and are shown in Table 2.

TABLE 2

Viscosities of Compositions 1 to 6 in accordance with the invention and Comparative Composition A.

| Formulation | A | 1 | 2 | 3 | 4 | 5 | 6 |
|---|---|---|---|---|---|---|---|
| Viscosity (cP) | 864 | 4889 | 2950 | 17343 | 17910 | 19113 | 6087 |

It will be seen that the comparative composition A, containing an AOS-CAPB combination at a wt ratio of 3:1, is too thin and shows minimal salt thickening response. In contrast, compositions in accordance with the invention show positive salt thickening over a range of surfactant ratios.

The invention claimed is:

1. A sulphate-free-surfactant cleansing composition comprising, in an aqueous continuous phase:
   a total amount of anionic surfactant and amphoteric surfactant consisting of:
   (i) from 3 wt % to 13 wt %, by weight of the total composition at 100% activity, of an alpha olefin sulfonate anionic surfactant of general formula (I):

$$R^1\text{—CH}=\text{CH—CH}_2\text{—SO}_3{}^-M^+ \qquad (I)$$

in which $R^1$ is selected from linear or branched alkyl groups having from 11 to 13 carbon atoms and mixtures thereof; and M is a solubilizing cation;
   (ii) from 1 to 8 wt %, by weight of amphoteric surfactant, which is cocamidopropyl betaine;
   (iii) from 0.05 wt % to 0.5 wt % of a cationic polymer;
   (iv) from 0.3 to 2.8 wt % an inorganic electrolyte; and
   (v) water;
   in which the weight ratio of (i) to (ii) ranges from 2:1 to 1:4 and the pH of the composition is from 3 to 6.5;
   wherein the composition has a viscosity of from 3,500 to 20,000 mPa·s, when measured using a TA Instruments Discovery Hybrid Rheometer; parallel 40 mm sandblasted plates, peak hold protocol at 4 s$^{-1}$; at 30° C.; and
   wherein the composition comprises no nonionic surfactants.

2. The composition according to claim 1, wherein the amount of alpha olefin sulfonate anionic surfactant of general formula (I) is from 2.5 to 12.85% by weight based on the total weight of the composition and at 100% activity.

3. The composition according to claim 1, in which the combined amount of
   (i) and (ii) ranges from 7 wt % to 15 wt % by total weight of the composition.

4. The composition according to claim 1, wherein the weight ratio of the alpha olefin sulfonate anionic surfactant (i) to the cocamidopropyl betaine (ii) is from 2:1 to 1:3.

5. The composition according to claim 1, wherein the cationic polymer is selected from Polyquaternium 10, guar hydroxypropyltrimethylammonium chlorides having a $M_w$ ranging from 800,000 to 2.5 million g/mol and a charge density ranging from 0.5 to 1.8 meq/g, and mixtures thereof.

6. The composition according to claim 1, wherein the inorganic electrolyte is selected from the group consisting of metal chlorides, metal sulfates, and mixtures thereof.

7. The composition according to claim 1, which has a viscosity of from 4,000 to 20,000 mPa·s, when measured using a TA Instruments Discovery Hybrid Rheometer; parallel 40 mm sandblasted plates, peak hold protocol at 4 s$^{-1}$; at 30° C.

8. The composition according to claim 1, which is transparent.

9. The composition according to claim 1, which is free from additional thickening agents selected from thickening polymers and visco-surfactants.

10. The composition according to claim 1 which comprises an isotropic surfactant phase.

11. The composition according to claim 1, which comprises an amount of inorganic electrolyte of from 0.5 to 2.3 wt % based on total weight of the composition, and wherein the weight ratio of (i) to (ii) is from 2:1 to 1:1.

12. A method of treating hair, scalp or skin comprising the step of applying to the hair, scalp or skin a composition as defined by claim 1.

13. The composition according to claim 2, wherein the amount of alpha olefin sulfonate anionic surfactant of general formula (I) is from 3.5 to 12% by weight based on the total weight of the composition and at 100% activity.

* * * * *